United States Patent
Weiner et al.

(10) Patent No.: US 11,007,265 B2
(45) Date of Patent: *May 18, 2021

(54) VACCINES HAVING AN ANTIGEN AND INTERLEUKIN-21 AS AN ADJUVANT

(71) Applicants: The Trustees of the University of Pennsylvania, Philadelphia, PA (US); Inovio Pharmaceuticals, Inc., Plymouth Meeting, PA (US)

(72) Inventors: David B. Weiner, Merion, PA (US); Matthew P. Morrow, Bala Cynwyd, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/181,594

(22) Filed: Nov. 6, 2018

(65) Prior Publication Data

US 2019/0060447 A1 Feb. 28, 2019

Related U.S. Application Data

(63) Continuation of application No. 15/514,948, filed as application No. PCT/US2015/052884 on Sep. 29, 2015, now Pat. No. 10,166,288.

(60) Provisional application No. 62/058,304, filed on Oct. 1, 2014.

(51) Int. Cl.
| | | |
|---|---|---|
| *A61K 39/39* | (2006.01) | |
| *A61K 39/08* | (2006.01) | |
| *A61K 39/12* | (2006.01) | |
| *A61K 39/21* | (2006.01) | |
| *A61K 41/00* | (2020.01) | |
| *A61N 1/32* | (2006.01) | |
| *C07K 14/54* | (2006.01) | |
| *A61K 39/00* | (2006.01) | |
| *A61K 48/00* | (2006.01) | |

(52) U.S. Cl.
CPC ............. *A61K 39/39* (2013.01); *A61K 39/08* (2013.01); *A61K 39/12* (2013.01); *A61K 39/21* (2013.01); *A61K 41/0047* (2013.01); *A61N 1/327* (2013.01); *C07K 14/54* (2013.01); *A61K 48/00* (2013.01); *A61K 2039/53* (2013.01); *A61K 2039/55527* (2013.01); *C12N 2740/16134* (2013.01); *Y02A 50/30* (2018.01)

(58) Field of Classification Search
CPC .... A61K 39/39; A61K 39/21; A61K 41/0047; A61K 39/08; A61K 39/12; A61K 48/00; A61K 2039/55527; A61K 2039/53; A61K 39/015; A61N 1/327; C07K 14/54; Y02A 50/30; C12N 2740/16134; A61P 43/00; A61P 37/04

See application file for complete search history.

(56) References Cited

U.S. PATENT DOCUMENTS

| | | | |
|---|---|---|---|
| 2005/0054726 A1 | 3/2005 | Thomsen | |
| 2005/0124044 A1* | 6/2005 | Cunningham | C07K 14/54 435/69.5 |
| 2006/0269973 A1* | 11/2006 | Yee | C12N 5/0636 435/7.23 |
| 2007/0212329 A1* | 9/2007 | Bruck | A61K 39/0011 424/85.2 |
| 2011/0002882 A1* | 1/2011 | Nelson | A61P 31/00 424/85.2 |
| 2012/0213815 A1* | 8/2012 | Weiner | A61P 31/16 424/199.1 |
| 2013/0052222 A1 | 2/2013 | Weiner et al. | |
| 2013/0195800 A1* | 8/2013 | Roeth | A61K 38/208 424/93.2 |
| 2013/0259924 A1 | 10/2013 | Bancel et al. | |

FOREIGN PATENT DOCUMENTS

| | | |
|---|---|---|
| JP | 2011037875 A | 2/2011 |
| WO | 2002/11748 A1 | 2/2002 |
| WO | 2003103589 | 12/2003 |
| WO | 2010103038 | 9/2010 |
| WO | 2011/119773 A1 | 9/2011 |
| WO | 2012/040266 A2 | 3/2012 |
| WO | 2013/151666 A2 | 10/2013 |

OTHER PUBLICATIONS

Li ZY, Chen J, Petersen E, Zhou DH, Huang SY, Song HQ, Zhu XQ. Synergy of mIL-21 and mIL-15 in enhancing DNA vaccine efficacy against acute and chronic Toxoplasma gondii infection in mice. Vaccine. May 23, 2014;32(25):3058-65. Epub Mar. 29, 2014.*

Feng C, Jin J, Zou Q, Chen X, Zhou C, Wu B, Weiner DB, Wang B. Interleukin-21 inhibits humoral response to an HIV DNA vaccine by enhancing BCL-6 and PAX-5 expression. Viral Immunol. Apr. 2012;25(2):131-40.*

Ramanathan MP, Kutzler MA, et. al, Weiner DB. Coimmunization with an optimized IL15 plasmid adjuvant enhances humoral immunity via stimulating B cells induced by genetically engineered DNA vaccines expressing consensus JEV and WNV E DIII. Vaccine. Jul. 9, 2009;27(32):4370-80. Epub Mar. 6, 2009.*

Yan J, Corbitt N, Pankhong P, Shin T, Khan A, Sardesai NY, Weiner DB. Immunogenicity of a novel engineered HIV-1 Glade C synthetic consensus-based envelope DNA vaccine. Vaccine. Sep. 22, 2011;29(41):7173-81. Epub Jun. 7, 2011.*

Lim KL, Jazayeri SD, Yeap SK, Alitheen NB, Bejo MH, Ideris A, Omar AR. Co-administration of avian influenza virus H5 plasmid DNA with chicken IL-15 and IL-18 enhanced chickens immune responses. BMC Vet Res. Aug. 6, 2012;8:132.*

(Continued)

*Primary Examiner* — Rachel B Gill
(74) *Attorney, Agent, or Firm* — Riverside Law LLP

(57) ABSTRACT

Disclosed herein is a vaccine comprising an antigen and IL-21. Also disclosed herein are methods for increasing an immune response in a subject. The methods may comprise administering the vaccine to the subject in need thereof.

16 Claims, 5 Drawing Sheets

Specification includes a Sequence Listing.

(56) References Cited

OTHER PUBLICATIONS

Kayamuro H, Yoshioka Y, Abe Y, et al. Interleukin-1 family cytokines as mucosal vaccine adjuvants for induction of protective immunity against influenza virus. J Virol. 2010;84(24):12703-12712.*
Bolesta E, Kowalczyk A, Wierzbicki A, et al. Increased level and longevity of protective immune responses induced by DNA vaccine expressing the HIV-1 Env glycoprotein when combined with IL-21 and IL-15 gene delivery. J Immunol. 2006;177(1):177-191. doi: 10.4049/jimmunol.177.1.177.*
Moroz A, Eppolito C, Li Q, Tao J, Clegg CH, Shrikant PA. IL-21 enhances and sustains CD8+ T cell responses to achieve durable tumor immunity: comparative evaluation of IL-2, IL-15, and IL-21. J Immunol. Jul. 15, 2004;173(2):900-9. (Year: 2004).*
Feng C, Jin J, Zou Q, Chen X, Zhou C, Wu B, Weiner DB, Wang B. Interleukin-21 inhibits humoral response to an HIV DNA vaccine by enhancing Bcl-6 and Pax-5 expression. Viral Immunol. Apr. 2012;25(2):131-40. (Year: 2012).*
Dou J, Tang Q, Zhao F, Chu L, Chen J, Cao M, Liu C, Wang Y, Li Y, Li JL. Comparison of immune responses induced in mice by vaccination with DNA vaccine constructs expressing mycobacterial antigen 85A and interleukin-21 and Bacillus Galmette-Guérin. Immunol Invest. 2008;37(2):113-27. (Year: 2008).*
Fröhlich A, Marsland BJ, Sonderegger I, Kurrer M, Hodge MR, Harris NL, Kopf M. IL-21 receptor signaling is integral to the development of Th2 effector responses in vivo. Blood. Mar. 1, 2007;109(5):2023-31. Epub Oct. 31, 2006. (Year: 2007).*
Varkey R, Du Q, Karnell JL, Xiao X, Casey KA, Woods R, Rosenthal K, Wilson S, Dall'Acqua WF, et. al. Discovery and characterization of potent IL-21 neutralizing antibodies via a novel alternating antigen immunization and humanization strategy. PLoS One. Jan. 25, 2019;14(1):e0211236. (Year: 2019).*
Cho HJ, Oh BM, Kim JT, Lim J, Park SY, Hwang YS, Baek KE, Kim BY, Choi I, Lee HG. Efficient Interleukin-21 Production by Optimization of Codon and Signal Peptide in Chinese Hamster Ovarian Cells. J Microbiol Biotechnol. Feb. 28, 2019;29(2):304-310. Year: 2019).*
Mauro VP, Chappell SA. A critical analysis of codon optimization in human therapeutics. Trends Mol Med. Nov. 2014;20(11):604-13. Epub Sep. 25, 2014. (Year: 2014).*
Dou J, Chen G, Wang J, Zhao F, Chen J, Fang X, Tang Q, Chu L. Preliminary study on mouse interleukin-21 application in tumor gene therapy. Cell Mol Immunol. Dec. 2004;1(6):461-6. (Year: 2004).*
Muthumani et al., "HIV-1 Env DNA Vaccine plus Protein Boost Delivered by EP Expands B- and T-Cell Responses and Neutralizing Phenotype In Vivo," 2013, PLoS ONE, 8:e84234.
Dou et al., "Comparison of Immune Responses Induced in Mice by Vaccination with Dna Vaccine Constructs Expressing Mycobacterial Antigen 85A and Interleukin-21 and Bacillus Galmette-Guerin," 2008, Immunological nvestigations, 37:113-127.
Skak et al., "Interleukin 21: combination strategies for cancer therapy," 2008, Nature Reviews, Drug Discovery, 7:231-240.
GenBank: BC066262.1. *Homo sapiens* interleukin 21, mRNA (cDNA clone MGC:79380 Image:6971866), complete cds. Dated Jul. 15, 2006.
GenBank: NP_068575.1: interleukin-21 isoform 1 precursor [*Homo sapiens*] Oct. 25, 2020, 3 pages.
He X et al., "Antitumor efficacy 0 viable tumor vaccine modified by heterogenetic ESAT-6 antigen and cytokine IL-21 in melanomatous mouse", Immunologic Research (2012) 52:240-249.
Hu K et al., 2011, "Immunization with DNA vaccine expressing herpes simplex virus type 1 gD and IL-21 protects against mouse herpes keratitis", Immunological Investigations, 40:265-278.
Yi JS et al., 2010, "Interleukin-21: A multifunctional regulator of immunity to infections", Microbes Infect., 12:1111-1119.

* cited by examiner

VACCINES HAVING AN ANTIGEN AND INTERLEUKIN-21 AS AN ADJUVANT

CROSS-REFERENCE TO RELATED APPLICATIONS

The present application is a continuation of U.S. patent application Ser. No. 15/514,948, filed on Mar. 28, 2017, which is the U.S. National State Application filed under 35 U.S.C. § 371 of International Patent Application No. PCT/US15/52884, filed Sep. 29, 2015, which claims priority from U.S. Provisional Application No. 62/058,304, filed Oct. 1, 2014, the entire disclosures of which are incorporated by reference herein in their entireties.

TECHNICAL FIELD

The present invention relates to vaccines comprising an antigen and IL-21, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Cytokines are proteins made by cells that affect the behavior of other cells, and unlike many adjuvants, can modulate specific immune responses. One such cytokine is the interleukin-21 (IL-21), which exerts actions on lymphoid and myeloid populations, as well as on epithelial cells, regulating both innate and adaptive immune responses. IL-21 has been shown to contribute to the functional differentiation of several CD4+ T cell subsets, to promote the proliferation and functional responses of CD8+ T cells, and to play a role in the development of B cell immunoglobulin responses. IL-21 is produced by CD8+ T cell populations as well as CD4+ T cell populations, including T follicular helper (TFH) cells, T helper type 17 (Th17) cells and natural killer T (NKT) cells.

Vaccines are also administered in many different ways (e.g., injection, orally, etc.) into many different tissues (e.g., intramuscular, intradermal, etc.). Not all delivery methods, however, are equal. Some delivery methods allow for greater compliance within a population of individuals while other delivery methods may affect the immunogenicity and/or safety of the vaccine. Accordingly, a need remains in the art for the development of safe and more effective adjuvants that increase antigenic responses irrespective of the identity of the antigen and route of administration.

SUMMARY OF THE INVENTION

The present invention is directed to a vaccine comprising an antigen and IL-21. IL-21 may be encoded by a nucleotide sequence selected from the group consisting of: a nucleotide sequence having at least about 95% identity to a nucleotide sequence as set forth in SEQ ID NO:3 and a nucleotide sequence as set forth in SEQ ID NO:3. IL-21 may be encoded by the nucleotide sequence as set forth in SEQ ID NO:3.

The antigen may be encoded by a first nucleic acid and IL-21 may be encoded by a second nucleic acid. The second nucleic acid may further comprise an expression vector. The vaccine may further comprise an antigen peptide with the same encoded nucleic acid sequence as the above antigen, and an IL-21 peptide with the same encoded nucleic acid sequence as the above IL-21.

The antigen may be selected from the group consisting of: a human papilloma virus (HPV) antigen, an Human Immunodeficiency Virus (HIV) antigen, an influenza antigen, a *Plasmodium falciparum* antigen, a *C. difficle* antigen, and a fragment thereof. The HPV antigen may be selected from the group consisting of: HPV16 E6 antigen, HPV16 E7 antigen, and a combination thereof. The HIV antigen may be selected from the group consisting of: Env A, Env B, Env C, Env D, B Nef-Rev, Gag, and any combination thereof. The influenza antigen may be selected from the group consisting of: H1 HA, H2 HA, H3 HA, H5 HA, BHA antigen, and any combination thereof. The *Plasmodium falciparum* antigen may include a circumsporozoite (CS) antigen. The *C. difficle* antigen may be selected from the group consisting of: Toxin A, Toxin B, and a combination thereof.

The vaccine may further comprise a pharmaceutically acceptable excipient.

The present invention is also directed to a method for increasing an immune response in a subject in need thereof. The method may comprise administering a vaccine comprising an antigen and IL-21. IL-21 may be encoded by a nucleotide sequence selected from the group consisting of: a nucleotide sequence having at least about 95% identity to a nucleotide sequence as set forth in SEQ ID NO:3 and a nucleotide sequence as set forth in SEQ ID NO:3. IL-21 may be encoded by the nucleotide sequence as set forth in SEQ ID NO:3.

Administering the vaccine may include electroporation. Increasing the immune response in the subject may include increasing a cellular immune response, a humoral immune response, or both a cellular and humoral immune response in subject.

The present invention is further directed to a nucleic acid molecule comprising one or more nucleotide sequences selected from the group consisting of: SEQ ID NO:3 and a nucleotide sequence that is 95% identical or greater to SEQ ID NO:3. The nucleic acid molecule may be a plasmid.

DETAILED DESCRIPTION

Figure 1:
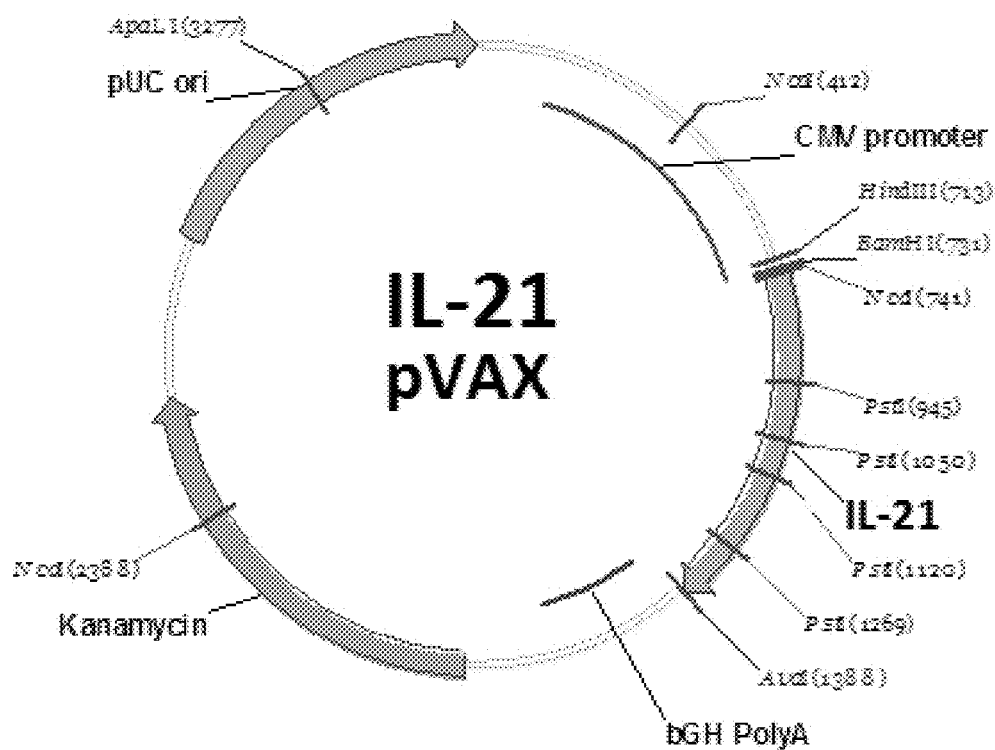
FIG. 1 shows a map of the plasmid pVAX-mIL-21 Opt, which includes optimized nucleic acids encoding for the mouse IL-21.

The present invention relates to vaccines that can be used to increase an immune response to an antigen in a subject by using IL-21 as an adjuvant. IL-21 is a single-chain, T-cell derived cytokine.

In some instances, IL-21 can function as a universal adjuvant because a greater immune response is elicited in the subject regardless of the source of the antigen or the route of administration as compared to a vaccine comprising the antigen alone. IL-21 may further augment the immune response of both viral and bacterial antigens, for example, HIV antigens and a *C. difficle* antigen, respectively. IL-21 may further be in the form of a DNA/peptide combination with an antigen that is a nucleic acid/peptide combination for a greater immune response vs. DNA or peptide alone with the antigen. In some instances, IL-21 can further augment the immune response in both muscle and skin tissues as demonstrated by increased interferon-γ (IFN-γ) production.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccines described herein to enhance the immunogenicity of the antigens.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" or "immunogenic fragment" as used herein means a nucleic acid sequence or a portion thereof that encodes a polypeptide capable of eliciting and/or increasing an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

Fragment or immunogenic fragment as used herein also means a polypeptide sequence or a portion thereof that is capable of eliciting and/or increasing an immune response in a mammal. The fragments can be polypeptide fragments selected from at least one of the various amino acid sequences set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of at least one of the proteins set forth below.

"Genetic construct" or "construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs or constructs that contain the necessary regulatory elements operably linked to a coding sequence that encodes a protein such that when present in the cell of the individual, the coding sequence will be expressed.

"Identical" or "identity" as used herein in the context of two or more nucleic acid or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of an antigen. The immune response can be in the form of a cellular or humoral immune response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to the cell, tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein or amino acid sequence set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus of the protein.

"Subject" as used herein can mean a mammal that wants to or is in need of being immunized with the herein described vaccines. The mammal can be a human, chimpanzee, dog, cat, horse, cow, mouse, or rat.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point $(T_m)$ for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. VACCINES

Provided herein is a vaccine comprising an antigen and an adjuvant. The vaccine can increase antigen presentation and the overall immune response to the antigen in an individual. The combination of antigen and adjuvant induces the immune system more efficiently than a vaccine comprising the antigen alone. The vaccine can further induce an immune response when administered to different tissues such as the muscle and the skin.

The vaccine of the present invention can have features required of effective vaccines such as being safe so that the vaccine itself does not cause illness or death; being protective against illness resulting from exposure to live pathogens such as viruses or bacteria; inducing neutralizing antibody to prevent infection of cells; inducing protective T cell responses against intracellular pathogens; and providing ease of administration, few side effects, biological stability, and low cost per dose. The vaccine can accomplish some or all of these features by combining the antigen with the adjuvant as discussed below.

a. Adjuvant

The vaccine can comprise an adjuvant and antigen as discussed below. The adjuvant can be a nucleic acid sequence, an amino acid sequence, or a combination thereof.

The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) IL-21

The adjuvant can be interleukin-21 (IL-21). IL-21 is a single chain, T-cell derived cytokine that has potent effects on B and T cell subsets including natural killer (NK) cells and cytotoxic T cells (CD8+ T cells). Animal models of chronic infection suggest a key role for IL-21 in T cell activity and control of viral replication, and in patients with chronic viral infections such as HIV. IL-21 has been reported to critically improve the cytotoxic CD8 T cell response. IL-21 has also been suggested to aid in B cell proliferation and differentiation.

IL-21, similar to IL-12, can stimulate IFN-γ production. IL-12 can activate naïve T cells to induce IFN-γ production while IL-21 can act on memory T cells to induce IFN-γ production. Inclusion of IL-21 in the vaccine can induce IFN-γ production by at least about 1.5-fold, at least about 2-fold, at least about 3-fold, at least about 4-fold, at least about 5-fold, at least about 8-fold, and at least about 10-fold as compared to a vaccine not including IL-23. Inclusion of IL-21 in the vaccine can induce IFN-γ production by at least about 2-fold as compared to a vaccine not including IL-21. Inclusion of IL-21 in the vaccine can induce IFN-γ production by at least about 3-fold as compared to a vaccine not including IL-21.

IL-21 can increase or boost the immune response to the antigen in a subject. The antigen is described in more detail below. In some instances, IL-21 can increase the immune response to the antigen by about 75% to about 200%. Alternatively, IL-21 can increase the immune response to the antigen by about 90% to about 130%. In still other alternative embodiments, IL-21 can increase the immune response to the antigen by about 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129% or 130%.

In other embodiments, IL-21 can increase or boost the immune response to the antigen by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold when the herein described vaccines are administered to a subject in need thereof.

A nucleic acid encoding IL-21 can be from any number of organisms, for example, mouse (Mus musculus) and human (Homo sapiens). The nucleic acid encoding IL-21 can be optimized with regards to codon usage and corresponding RNA transcripts. The nucleic acid encoding IL-21 can be codon and RNA optimized for expression. In some embodiments, the nucleic acid encoding IL-21 can include a Kozak sequence (e.g., GCC ACC) to increase the efficiency of translation. The nucleic acid encoding IL-21 can include multiple stop codons (e.g., TGA TGA) to increase the efficiency of translation termination. The nucleic acid encoding IL-21 can also include a nucleotide sequence encoding a IgE leader sequence. The IgE leader sequence can be located 5' to IL-21 in the nucleic acid. In some embodiments, the nucleic acid encoding IL-21 is free of or does not contain a nucleotide sequence encoding the IgE leader sequence. In other embodiments, the nucleic acid encoding IL-21 can include a nucleotide sequence encoding an HA tag (SEQ ID NO:9). In still other embodiments, the nucleic acid encoding IL-21 is free of or does not contain a nucleotide sequence encoding the HA tag.

The mouse IL-21 can be the optimized nucleic acid sequence SEQ ID NO: 1, which encodes SEQ ID NO:2. In some embodiments, the mouse IL-21 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO: 1. In other embodiments, the mouse IL-21 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2. The mouse IL-21 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 2.

The human IL-21 can be the optimized nucleic acid sequence SEQ ID NO: 3, which encodes for SEQ ID NO:4. In some embodiments, the human IL-21 can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the nucleic acid sequence set forth in SEQ ID NO: 3. In other embodiments, the human IL-21 can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 4. The human IL-21 can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO: 4.

Some embodiments relate to fragments of SEQ ID NO:1 and/or SEQ ID NO:3. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1 and/or SEQ ID NO:3. In some embodiments, fragments can include sequences that encode a leader sequence, for example, an immunoglobulin leader sequence, such as the IgE leader sequence. In some embodiments, fragments are free of coding sequences that encode a leader sequence.

Fragments of nucleic acids with nucleotide sequences having identity to fragments of SEQ ID NO:1 and/or SEQ ID NO:3 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NO:1 and/or SEQ ID NO:3. Some embodiments relate to fragments that have 96% or greater identity to the fragments of IL-21 nucleic acid sequences herein. Some embodiments relate to fragments that have 97% or greater identity to the fragments of IL-21 nucleic acid sequences herein. Some embodiments relate to fragments that have 98% or greater identity to the fragments of IL-21 nucleic acid sequences herein. Some embodiments relate to fragments that have 99% or greater identity to the fragments of IL-21 nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NO:2 and/or SEQ ID NO:4 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2 and/or SEQ ID NO:4. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NO:2 and/or SEQ ID NO:4 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NO:2 and/or SEQ ID NO:4. Some embodiments relate to fragments having 96% or greater identity to the fragments of IL-21 protein sequences herein. Some embodiments relate to fragments having 97% or greater identity to the fragments of IL-21 protein sequences herein. Some embodiments relate to fragments having 98% or greater identity to the fragments of IL-21 protein sequences herein. Some embodiments relate to fragments having 99% or greater identity to the fragments of IL-21 protein sequences herein. In some embodiments, fragments include a leader sequence, for example, an immunoglobulin leader sequence such as the IgE leader sequence. In some embodiments, the fragments are free of a leader sequence.

b. Antigen

The vaccine can comprise an antigen or fragment or variant thereof and an adjuvant as discussed above. The antigen can be anything that induces an immune response in a subject. Purified antigens are not usually strongly immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject. In other embodiments, the combination of the adjuvant and the antigen can boost or increase a humoral immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). As discussed below, the antigen of the vaccine can be selected from a group consisting of an HIV antigen, a *C. difficile* antigen, and a fragment thereof. The HIV antigen can be selected from the group consisting of Env A, Env B, Env C, Env D, B Nef-Rev, Gag, and any combination thereof.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

(a) Hepatitis Antigen

IL-21 can be associated or combined with a hepatitis virus antigen (i.e., hepatitis antigen), or fragment thereof, or variant thereof. The hepatitis antigen can be an antigen or immunogen from hepatitis A virus (HAV), hepatitis B virus (HBV), hepatitis C virus (HCV), hepatitis D virus (HDV), and/or hepatitis E virus (HEV). In some embodiments, the hepatitis antigen can be a heterologous nucleic acid molecule(s), such as a plasmid(s), which encodes one or more of the antigens from HAV, HBV, HCV, HDV, and HEV. The hepatitis antigen can be full-length or immunogenic fragments of full-length proteins.

The hepatitis antigen can comprise consensus sequences and/or one or more modifications for improved expression. Genetic modifications, including codon optimization, RNA optimization, and the addition of a highly efficient immunoglobulin leader sequence to increase the immunogenicity of the constructs, can be included in the modified consensus sequences. The consensus hepatitis antigen may comprise a signal peptide such as an immunoglobulin signal peptide such as an IgE or IgG signal peptide, and in some embodiments, may comprise an HA tag. The immunogens can be designed to elicit stronger and broader cellular immune responses than corresponding codon optimized immunogens.

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof. The hepatitis antigen can be a consensus HBV core protein, or a consensus HBV surface protein.

In some embodiments, the hepatitis antigen can be a HBV genotype A consensus core DNA sequence construct, an IgE leader sequence linked to a consensus sequence for HBV genotype A core protein, or a HBV genotype A consensus core protein sequence.

In other embodiments, the hepatitis antigen can be a HBV genotype B consensus core DNA sequence construct, an IgE leader sequence linked to a consensus sequence for HBV genotype B core protein, or a HBV genotype B consensus core protein sequence.

In still other embodiments, the hepatitis antigen can be a HBV genotype C consensus core DNA sequence construct, an IgE leader sequence linked to a consensus sequence for HBV genotype C core protein, or a HBV genotype C consensus core protein sequence.

In some embodiments, the hepatitis antigen can be a HBV genotype D consensus core DNA sequence construct, an IgE leader sequence linked to a consensus sequence for HBV genotype D core protein, or a HBV genotype D consensus core protein sequence.

In other embodiments, the hepatitis antigen can be a HBV genotype E consensus core DNA sequence construct, an IgE leader sequence linked to a consensus sequence for HBV genotype E core protein, or a HBV genotype E consensus core protein sequence.

In some embodiments, the hepatitis antigen can be a HBV genotype F consensus core DNA sequence construct, an IgE leader sequence linked to a consensus sequence for HBV genotype F core protein, or a HBV genotype F consensus core protein sequence.

In other embodiments, the hepatitis antigen can be a HBV genotype G consensus core DNA sequence construct, an IgE leader sequence linked to a consensus sequence for HBV genotype G core protein, or a HBV genotype G consensus core protein sequence.

In some embodiments, the hepatitis antigen can be a HBV genotype H consensus core DNA sequence construct, an IgE leader sequence linked to a consensus sequence for HBV genotype H core protein, or a HBV genotype H consensus core protein sequence.

In still other embodiments, the hepatitis antigen can be a HBV genotype A consensus surface DNA sequence construct, an IgE leader sequence linked to a consensus sequence for HBV genotype A surface protein, or a HBV genotype A consensus surface protein sequence.

In some embodiments, the hepatitis antigen can be a HBV genotype B consensus surface DNA sequence construct, an IgE leader sequence linked to a consensus sequence for HBV genotype B surface protein, or a HBV genotype B consensus surface protein sequence.

In other embodiments, the hepatitis antigen can be a HBV genotype C consensus surface DNA sequence construct, an IgE leader sequence linked to a consensus sequence for HBV genotype C surface protein, or a HBV genotype C consensus surface protein sequence.

In still other embodiments, the hepatitis antigen can be a HBV genotype D consensus surface DNA sequence construct, an IgE leader sequence linked to a consensus sequence for HBV genotype D surface protein, or a HBV genotype D consensus surface protein sequence.

In some embodiments, the hepatitis antigen can be a HBV genotype E consensus surface DNA sequence construct, an IgE leader sequence linked to a consensus sequence for HBV genotype E surface protein, or a HBV genotype E consensus surface protein sequence.

In other embodiments, the hepatitis antigen can be a HBV genotype F consensus surface DNA sequence construct, an IgE leader sequence linked to a consensus sequence for HBV genotype F surface protein, or a HBV genotype F consensus surface protein sequence.

In still other embodiments, the hepatitis antigen can be a HBV genotype G consensus surface DNA sequence construct, an IgE leader sequence linked to a consensus sequence for HBV genotype G surface protein, or a HBV genotype G consensus surface protein sequence.

In other embodiments, the hepatitis antigen can be a HBV genotype H consensus surface DNA sequence construct, an IgE leader sequence linked to a consensus sequence for HBV genotype H surface protein, or a HBV genotype H consensus surface protein sequence.

(b) Human Papilloma Virus (HPV) Antigen

IL-21 can be associated or combined with a human papilloma virus (HPV) antigen, or fragment thereof, or variant thereof. The HPV antigen can be from HPV types 16, 18, 31, 33, 35, 45, 52, and 58, which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(c) RSV Antigen

IL-21 can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be consensus RSV F amino acid sequence, or fragment or variant thereof. The RSV antigen can be an optimized nucleic acid encoding RSV F amino acid sequence or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be a consensus RSV G amino acid sequence, or fragment or variant thereof. The RSV antigen can be an optimized nucleic acid encoding RSV G amino acid sequence or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have a consensus amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the consensus RSV G amino acid sequence, the optimized nucleic acid encoding RSV G amino acid sequence, the human RSV genome of the RSV Long strain, the consensus RSV F amino acid sequence, the optimized nucleic acid encoding RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, for the RSV M2-2 protein from the RSV Long strain, the RSV L protein from the RSV Long strain, the RSV G protein from the RSV subtype B isolate H5601, the RSV G protein from the RSV subtype B isolate H1068, for the RSV G protein from the RSV subtype B isolate H5598, the RSV G protein from the RSV subtype B isolate H1123, or fragment thereof, or variant thereof.

(d) Influenza Antigen

IL-21 can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen comprising a consensus H1 amino acid sequence or a consensus H2 amino acid sequence. The consensus hemagglutinin antigen may be a synthetic hybrid consensus H1 sequence comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminus, an IgE or IgG leader amino acid sequence. The consensus hemagglutinin antigen may further comprise an immunogenic tag, which is a unique immunogenic epitope that can be detected by readily available antibodies. An example of such an immunogenic tag is the 9 amino acid influenza HA Tag, which may be linked on the consensus hemagglutinin C-terminus. In some embodiments, consensus hemagglutinin antigen may further comprise on its N-terminus, an IgE or IgG leader amino acid sequence and on its C-terminus, an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or a an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C-terminus of the protein and the sequence encoding it is 3' of the consensus HA coding sequence. The immunogenic tag provides a unique epitope for which there are readily available antibodies so that such antibodies can be used in assays to detect and confirm expression of the protein. The immunogenic tag can be an HA Tag at the C-terminus of the protein.

(e) Human Immunodeficiency Virus (HIV) Antigen

IL-21 can be associated or combined with an HIV antigen or fragment thereof, or variant thereof. HIV antigens can include modified consensus sequences for immunogens. Genetic modifications, including codon optimization, RNA optimization, and the addition of a highly efficient immunoglobin leader sequence to increase the immunogenicity of constructs, can be included in the modified consensus sequences. The novel immunogens can be designed to elicit stronger and broader cellular immune responses than a corresponding codon optimized immunogen.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be Acanthamoeba, Anisakis, *Ascaris lumbricoides*, Botfly, *Balantidium coli*, Bedbug, *Cestoda* (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa loa, Paragonimus*—lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

IL-21 can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS; LSA1; TRAP; CelTOS; and Ama1. The immunogens may be full length or immunogenic fragments of full length proteins. The immunogens can comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA Tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA Tag.

In further embodiments, the malaria antigen can be Ama1, which is a highly conserved *Plasmodium* antigen. The malaria antigen can also be a consensus sequence of Ama1 (i.e., ConAma1 immunogen) comprising in some instances, a signal peptide such as an immunoglobulin signal peptide such as an IgE or IgG signal peptide and in some embodiments, may comprise an HA Tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA Tag.

In other embodiments, the malaria antigen can be a fusion protein comprising a combination of two or more of the PF proteins set forth herein. For example, fusion proteins may comprise two or more of Consensus CS immunogen, ConLSA1 immunogen, ConTRAP immunogen, ConCelTOS immunogen and ConAma1 immunogen linked directly adjacent to each other or linked with a spacer or one more amino acids in between. In some embodiments, the fusion protein comprises two PF immunogens. In some embodiments the fusion protein comprises three PF immunogens. In some embodiments, the fusion protein comprises four PF immunogens. In some embodiments the fusion protein comprises five PF immunogens.

Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N-terminus. In some embodiments, the fusion proteins comprise multiple signal peptides linked to the N-terminus of each Consensus PF immunogen. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein, wherein the spacer is a proteolyic cleavage site recognized by a protease found in cells to which the vaccine is intended to be administered and/or taken up and the fusion protein comprises multiple signal peptides linked to the N-terminus of each Consensus PF immunogens such that upon cleavage, the signal peptide of each Consensus PF immunogen translocates the respective Consensus PF immunogen to outside of the cell.

(3) Bacterial Antigens

The antigen can be bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, psychrophile, halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthraces*, methicillin-resistant *Staphylococcus aureus* (MRSA), or *Clostridium difficile*.

(a) *Mycobacterium tuberculosis* Antigens

IL-21 can be associated or combined with a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

In some embodiments, the TB antigen can be heterologous nucleic acid molecules such as plasmids, which encode one or more of the *Mycobacterium tuberculosis* immunogens from the Ag85 family and the Esx family. The immunogens can be full-length or immunogenic fragments of full-length proteins. The immunogens can comprise consensus sequences and/or modifications for improved expression. Consensus immunogens may comprise a signal peptide such as an immunoglobulin signal peptide such as an IgE or IgG signal peptide and in some embodiments, may comprise an HA tag.

(b) *Clostridium difficile* Antigens

IL-21 can be associated or combined with a *Clostridium difficile* antigen (i.e., CD antigen or CD immunogen), or fragment thereof, or variant thereof. The CD antigen can be Toxin A or Toxin B. In some embodiments, the CD antigen can be heterologous nucleic acid molecules such as plasmids, which encode Toxin A, Toxin B, or both Toxin A and Toxin B. The CD antigen can be full-length proteins or immunogenic fragments of full-length proteins. The CD antigen can comprise consensus sequences and/or modifications for improved expression. The CD antigen can comprise a signal peptide such as an immunoglobulin signal peptide, for example, an IgE or IgG signal peptide, and in some embodiments, can comprise an HA tag.

(4) Fungal Antigens

The antigen can be a fungal antigen or fragment or variant thereof. The fungus can be *Aspergillus* species, *Blastomyces dermatitides, Candida* yeasts (e.g., *Candida albicans*), *Coccidioides, Cryptococcus neoformans, Cryptococcus gattii*, dermatophyte, *Fusarium* species, *Histoplasma capsulatum, Mucoromy cotina, Pneumocystis jirovecii, Sporothrix schenckii, Exserohilum*, or *Cladosporium*.

c. Vector

The vaccine can comprise one or more vectors that include one or more heterologous nucleic acids encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular heterologous nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing heterologous DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, and/or one or more desired adjuvants. The LEC may be any linear DNA devoid of any phosphate backbone. The DNA may encode one or more antigens, and/or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The LEC may be derived from any plasmid capable of being linearized. The plasmid may be capable of expressing the antigen, and/or the adjuvant. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than IL-21, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent can be a polyanion, polycation, including poly-L-glutamate (LGS), or lipid. The transfection facilitating agent can be poly-L-glutamate, and the poly-L-glutamate can be present in the vaccine at a concentration of less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene. Hyaluronic acid can also be used or administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to IL-21. The additional adjuvant can be other genes that are expressed in an alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to IL-21 include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. Methods of Vaccination

The present invention is also directed to methods of increasing an immune response in a subject by different routes of administration of the vaccine. Increasing the immune response can be used to treat and/or prevent disease in the subject.

The method can include administering the herein disclosed vaccines to the subject. The subject administered the vaccine can have an increased or boosted immune response as compared to a subject administered the antigen alone. In some embodiments, the immune response in the subject administered the vaccine can be increased by about 18% to about 650%. Alternatively, the immune response in the subject administered the vaccine may be increased by about 45% to about 260%. In still other alternative embodiments, the immune response in the subject administered the vaccine may be increased by about 93% to about 130%.

In other embodiments, the administered vaccine can increase or boost the immune response in the subject by at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccines can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241, 701; 6,233,482; 6,216,034; 6,208,893; 6,192,270; 6,181, 964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520, 950; 7,171,264; 6,208,893; 6,009,347; 6,120,493; 7,245, 963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example, set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired, means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could, for example, be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

3. EXAMPLES

Example 1

Expression of IL-21

A plasmid (i.e., pVAX-mIL-21 Opt) encoding the IL-21 gene was constructed for expression of IL-21 (FIG. 1). The DNA sequence of IL-21 was codon and RNA optimized before insertion into the plasmid.

Figure 2:
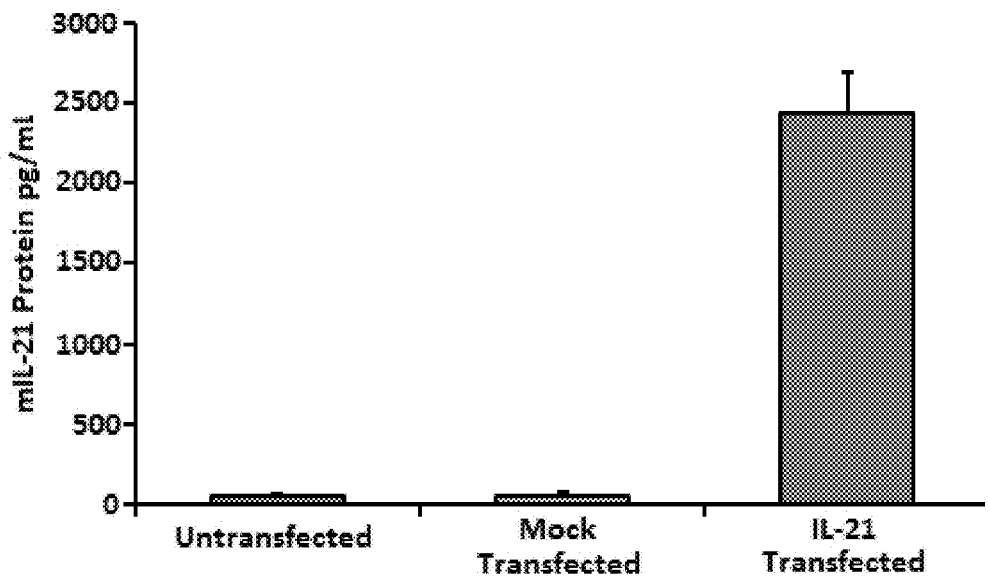
FIG. 2 shows expression of IL-21 in supernatants from transfected HEK 293T cells.
Figure 3:
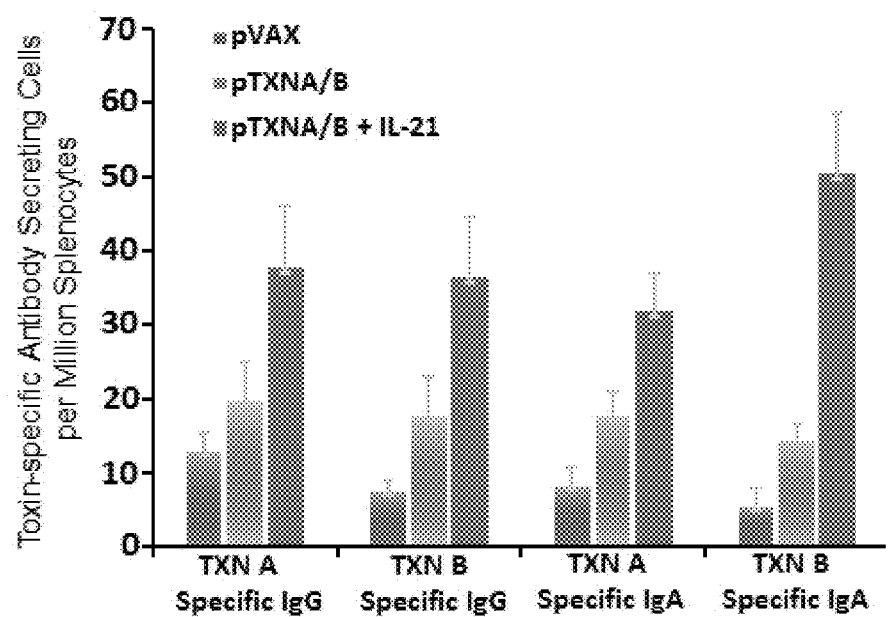
FIG. 3 shows the humoral immune response in mice, immunized via an intramuscular route with plasmids encoding Toxin A and Toxin B antigens from *C. difficle*, using a B cell ELISpot assay.

The plasmid was transfected into HEK 293T cells to confirm IL-21 expression. Cell supernatants were analyzed by ELISA. The results showed that the IL-21 was expressed in the HEK 293T cells (FIG. 2).

Example 2

IL-21 Increased IgG and IgA Serum Titers

Mice were used as a model system to determine whether IL-21 could function as an adjuvant when the vaccine was administered via an intramuscular route. The vaccine included Toxin A and Toxin B antigens from *C. difficle* and IL-21, of which were encoded by respective plasmids.

Specifically, a group of mice were immunized with the plasmid pVAX-mIL-21 Opt (FIG. 1 and described above in Example 1) and plasmids encoding the Toxin A and Toxin B antigens from *C. difficle* as described above. A second group of mice were immunized only with the plasmids encoding the Toxin A and Toxin B antigens. A third group of mice were immunized only with the empty control plasmid pVAX. Mice were immunized by the intramuscular route using electroporation. Circulating antigen-specific IgG and IgA antibody secreting cells were next analyzed in the blood of immunized animals to determine the influence of the IL-21 adjuvant.

Figure 4:
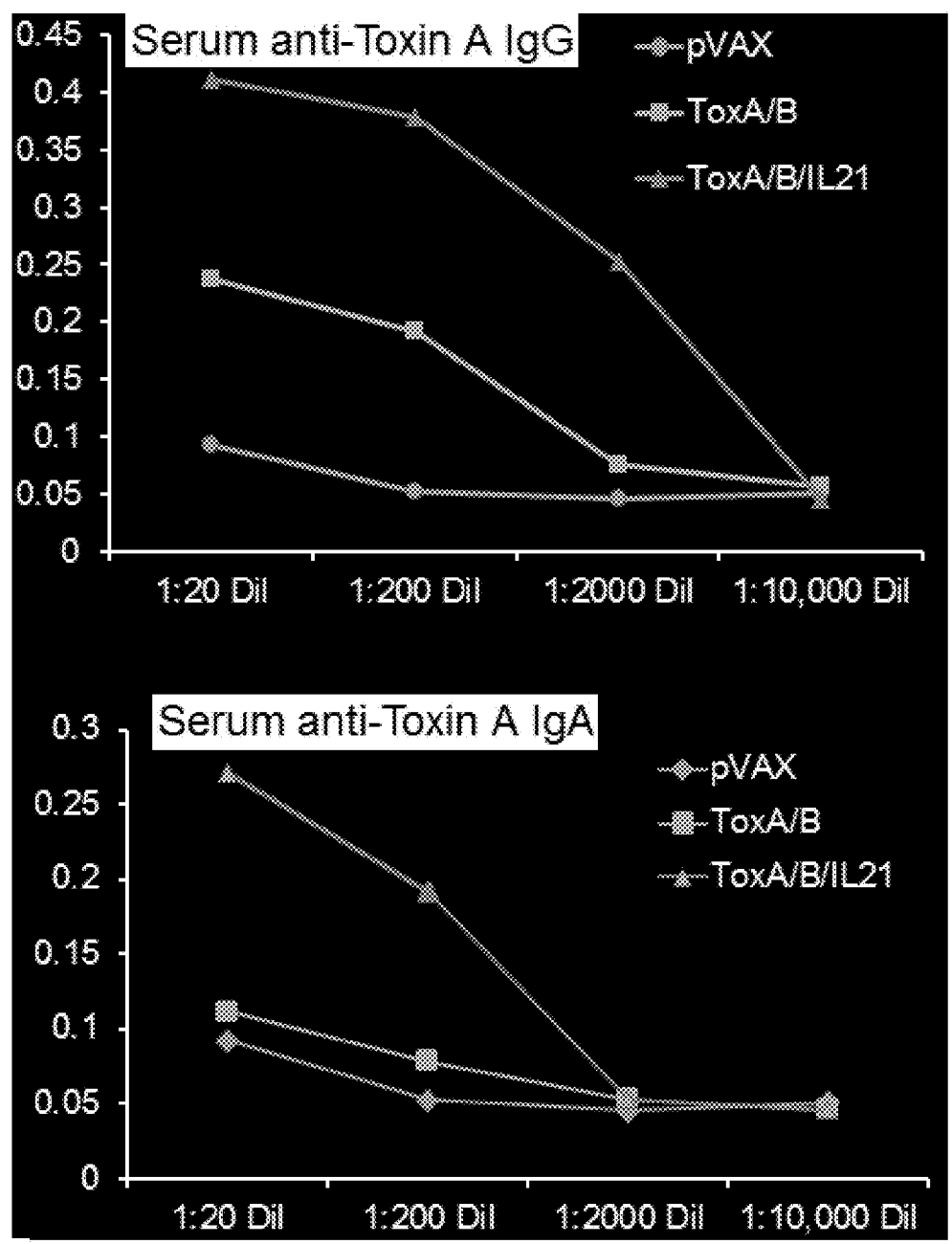
FIG. 4 shows the humoral immune response in mice, immunized via an intramuscular route, using an ELISA assay.

As shown in the upper panel of FIG. 4, the IL-21 adjuvant increased the total amount of serum anti-Toxin A IgG as compared with immunization with antigen alone, with robust titers seen at the 1:2000 dilution in the IL-21 group, but not the group receiving antigen only. When serum IgA was analyzed, it was noted that the inclusion of the IL-21 adjuvant resulted in a detectable level of antigen-specific IgA that tittered out at a 1:2000 dilution, whereas immunization with antigen alone did not show any robust signal over naïve animals (FIG. 4 lower panel).

The above data showed that IL-21 has the ability to function as an adjuvant when administered by an intramuscular route because IL-21 augmented the humoral immune response to the Toxin A and Toxin B antigens from *C. difficle*. The above data also indicated that IL-21 is able to function as an adjuvant with a bacterial antigen.

Example 3

IL-21 Increased the Cellular and Humoral Immune Responses to HIV Antigens

IL-21 adjuvant was also administered in combination with plasmids encoding the EnvA and EnvC antigens from HIV. The inclusion of IL-21 in the vaccine augmented both the cellular and humoral immune responses to EnvC. The vaccine included EnvA and EnvC antigens from HIV and IL-21. The EnvA antigen, EnvC antigen and IL-21 were encoded by separate plasmids.

Specifically, the EnvA antigen was a consensus protein (SEQ ID NO:6), which was encoded by the nucleotide sequence set forth in SEQ ID NO:5. This nucleotide sequence set forth in SEQ ID NO:5 was incorporated into a plasmid.

The EnvC antigen was a consensus protein (SEQ ID NO:8), which was encoded by the nucleotide sequence set forth in SEQ ID NO:7. This nucleotide sequence set forth in SEQ ID NO:7 was incorporated into a plasmid.

Specifically, a group of mice were immunized with the plasmid pVAX-mIL-21 Opt (FIG. 1 and described above in Example 1) and a plasmid encoding the EnvA and EnvC antigens as described above. A second group of mice were immunized only with the plasmids encoding the EnvA and EnvC antigens. A third group of mice were immunized only with the empty control plasmid pVAX. Mice were immunized via an intramuscular route using electroporation. An Interferon Gamma ELISpot assay was used to examine the cellular immune response in the immunized groups of mice.

Figure 5:
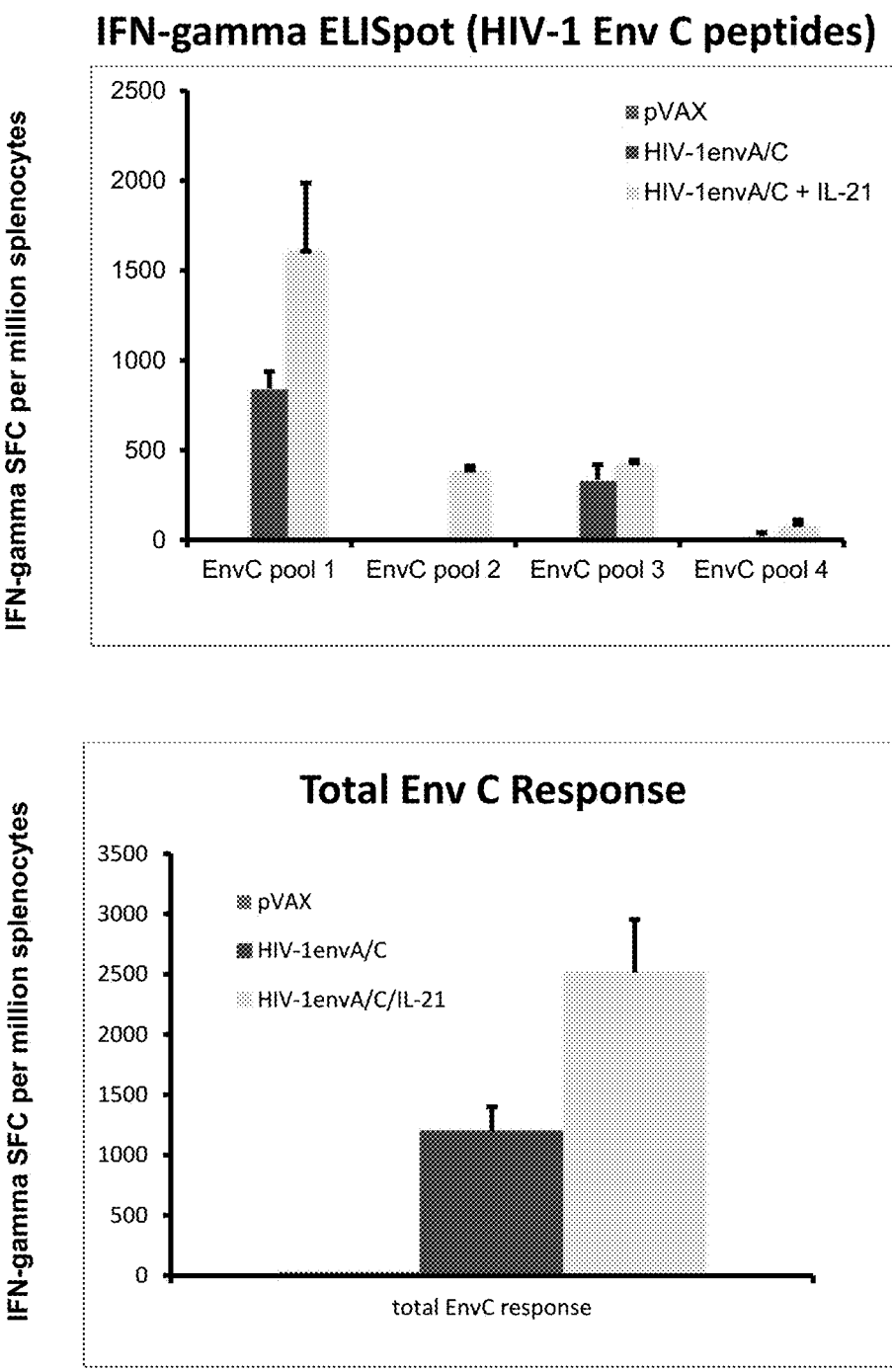
FIG. 5 shows the cellular immune response in mice, immunized via an intramuscular route with plasmids encoding EnvA and EnvC antigens from HIV, using an Interferon Gamma ELISpot assay.

As shown in FIG. 5, immunization with IL-21 increased the cellular immune response by greater than 2-fold to the EnvC antigen as compared to antigens alone. Accordingly, these data indicated that IL-21 is able to function as an adjuvant in muscle tissue because IL-21 augmented the cellular immune response to the EnvA and EnvC antigens.

Figure 6:
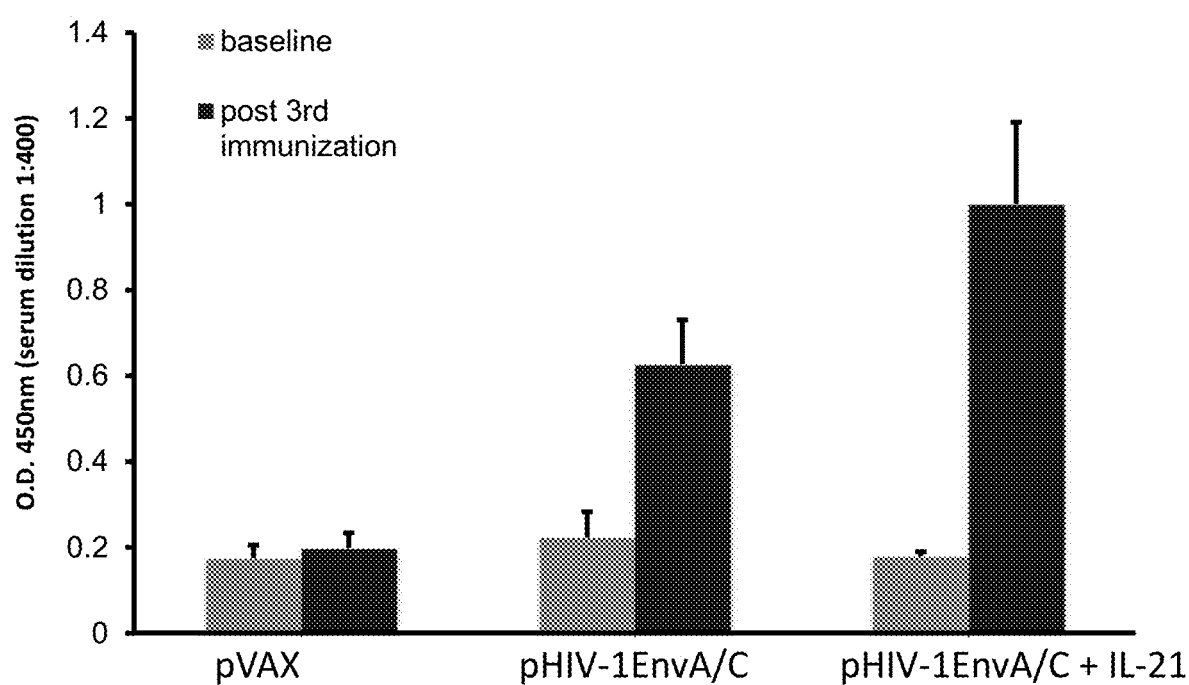
FIG. 6 shows the humoral immune response in mice, immunized via an intramuscular route with plasmids encoding EnvA and EnvC antigens from HIV, using an ELISA assay.

Antibody responses were measured in the sera of immunized animals following the third immunization by ELISA against EnvA protein (FIG. 6). At a 1:400 dilution, the average O.D. of HIV EnvA/C was approximately 0.6, whereas the IL-21 adjuvant group had an average O.D. reading of 1.0.

Taken together these data suggest that IL-21 exerts novel adjuvant activity in the form of increased frequency of antibody secreting cells, the amount of IgG produced and class switching, increases in the amount of IgA production, and increased IFN-gamma secretion when included in a DNA vaccine.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising:
   a) at least one selected from the group consisting of an antigen and a nucleic acid molecule encoding an antigen; and
   b) a nucleic acid molecule comprising a nucleotide sequence encoding IL-21, wherein the nucleotide sequence comprises a nucleotide sequence selected from the group consisting of: SEQ ID NO: 3 and a nucleotide sequence that is 90% identical or greater to SEQ ID NO: 3.

2. The immunogenic composition of claim 1, wherein the antigen is encoded by a first nucleic acid and IL-21 is encoded by a second nucleic acid.

3. The immunogenic composition of claim 2, further comprising an antigen peptide encoded by the same nucleic acid sequence as the antigen of claim 2, and an IL-21 peptide encoded by the same encoded nucleic acid sequence as IL-21 of claim 2.

4. The immunogenic composition of claim 2, wherein the second nucleic acid further comprises an expression vector.

5. The immunogenic composition of claim 1, wherein the antigen is selected from the group consisting of: a human papilloma virus (HPV) antigen, an Human Immunodeficiency Virus (HIV) antigen, an influenza antigen, a *Plasmodium falciparum* antigen, a *C. difficle* antigen, and a fragment thereof.

6. The immunogenic composition of claim 5, wherein the HPV antigen is selected from the group consisting of: HPV16 E6 antigen, HPV16 E7 antigen, and a combination thereof.

7. The immunogenic composition of claim 5, wherein the HIV antigen is selected from the group consisting of: Env A, Env B, Env C, Env D, B Nef-Rev, Gag, and any combination thereof.

8. The immunogenic composition of claim 5, wherein the influenza antigen is selected from the group consisting of: H1 HA, H2 HA, H3 HA, H5 HA, BHA antigen, and any combination thereof.

9. The immunogenic composition of claim 5, wherein the *Plasmodium falciparum* antigen includes a circumsporozoite (CS) antigen.

10. The immunogenic composition of claim 5, wherein the *C. difficle* antigen is selected from the group consisting of: Toxin A, Toxin B, and a combination thereof.

11. The immunogenic composition of claim 1, further comprising a pharmaceutically acceptable excipient.

12. A method for increasing an immune response in a subject in need thereof, the method comprising administering the immunogenic composition of claim 1 to the subject.

13. The method of claim 12, wherein administering the immunogenic composition includes electroporation.

14. The method of claim 12, wherein increasing the immune response in the subject includes increasing a cellular immune response, a humoral immune response, or both a cellular and humoral immune response in subject.

15. A nucleic acid molecule comprising one or more nucleotide sequences selected from the group consisting of: SEQ ID NO:3 and a nucleotide sequence that is 90% identical or greater to SEQ ID NO:3.

16. The nucleic acid molecule of claim 15, wherein the nucleic acid molecule is a plasmid.

* * * * *

SEQUENCE LISTING

```
<160> NUMBER OF SEQ ID NOS: 9

<210> SEQ ID NO 1
<211> LENGTH: 495
<212> TYPE: DNA
<213> ORGANISM: Artificial Sequence
<220> FEATURE:
<223> OTHER INFORMATION: chemically synthesized

<400> SEQUENCE: 1
atggactgga cctggatcct gttcctggtc gccgcagcca caagggtgca cagcgagagg      60
accctggtct gcctggtggt gatcttcctg ggcaccgtgg cccacaagag cagcccccag     120
ggccccgaca ggctgctgat caggctgagg cacctgatcg acatcgtgga gcagctgaag     180
atctacgaga acgacctgga ccccgagctg ctctccgccc ctcaagacgt gaagggccac     240
tgcgagcacg ccgccttcgc ctgcttccag aaggccaagc tgaagcccag caaccccggc     300
aacaacaaga ccttcatcat cgacctggtg gcccagctga agaaggct gcccgccaga       360 aggggcggca agaagcagaa acacatcgcc aagtgcccca gctgcgacag ctacgagaag     420
aggaccccca aggaatttct ggagaggctg aagtggctgc tgcagaagat gattcaccag     480
cacctgagct gatga                                                     495

<210> SEQ ID NO 2
<211> LENGTH: 163
<212> TYPE: PRT
<213> ORGANISM: Artificial Sequence
<220> FEATURE:
<223> OTHER INFORMATION: chemically synthesized

<400> SEQUENCE: 2

Met Asp Trp Thr Trp Ile Leu Phe Leu Val Ala Ala Ala Thr Arg Val
1               5                   10                  15

His Ser Glu Arg Thr Leu Val Cys Leu Val Val Ile Phe Leu Gly Thr
            20                  25                  30

Val Ala His Lys Ser Ser Pro Gln Gly Pro Asp Arg Leu Leu Ile Arg
        35                  40                  45

Leu Arg His Leu Ile Asp Ile Val Glu Gln Leu Lys Ile Tyr Glu Asn
    50                  55                  60

Asp Leu Asp Pro Glu Leu Leu Ser Ala Pro Gln Asp Val Lys Gly His
65                  70                  75                  80

Cys Glu His Ala Ala Phe Ala Cys Phe Gln Lys Ala Lys Leu Lys Pro
                85                  90                  95
```

Ser Asn Pro Gly Asn Asn Lys Thr Phe Ile Ile Asp Leu Val Ala Gln
            100                 105                 110

Leu Arg Arg Arg Leu Pro Ala Arg Arg Gly Gly Lys Lys Gln Lys His
        115                 120                 125

Ile Ala Lys Cys Pro Ser Cys Asp Ser Tyr Glu Lys Arg Thr Pro Lys
130                 135                 140

Glu Phe Leu Glu Arg Leu Lys Trp Leu Leu Gln Lys Met Ile His Gln
145                 150                 155                 160

His Leu Ser

<210> SEQ ID NO 3
<211> LENGTH: 537
<212> TYPE: DNA
<213> ORGANISM: Artificial Sequence
<220> FEATURE:
<223> OTHER INFORMATION: chemically synthesized

<400> SEQUENCE: 3
atggactgga cttggattct gtttctggtc gcagcagcaa ctagagtgca ttcacgcagc      60
agccctggga acatggagag gattgtcatc tgcctgatgg tgattttcct gggcacactg     120
gtccacaaga gctcctctca gggacaggac aggcatatga tcaggatgcg acagctgatc     180
gacatcgtgg atcagctgaa gaactacgtg aacgacctgg tcccagagtt tctgcctgca     240
ccagaggatg tcgaaactaa ctgcgaatgg agtgccttct catgtttcca gaaggcacag     300
ctgaagtccg ctaacaccgg aaacaatgag cgaatcatca acgtgagcat taagaaactg     360
aagcgaaagc cccctagtac caatgctggc cggagacaga gcacagact  gacatgccct     420 agctgtgatt cctacgaaaa gaaaccaccc aaggagttcc tggaacgctt aaaagcctg     480 ctgcagaaaa tgattcacca gcacctgtct tccagaaccc acggctcaga ggattca      537

<210> SEQ ID NO 4
<211> LENGTH: 179
<212> TYPE: PRT
<213> ORGANISM: Artificial Sequence
<220> FEATURE:
<223> OTHER INFORMATION: chemically synthesized

<400> SEQUENCE: 4

Met Asp Trp Thr Trp Ile Leu Phe Leu Val Ala Ala Ala Thr Arg Val
1               5                   10                  15

His Ser Arg Ser Ser Pro Gly Asn Met Glu Arg Ile Val Ile Cys Leu
            20                  25                  30

Met Val Ile Phe Leu Gly Thr Leu Val His Lys Ser Ser Ser Gln Gly
        35                  40                  45

Gln Asp Arg His Met Ile Arg Met Arg Gln Leu Ile Asp Ile Val Asp
50                  55                  60

Gln Leu Lys Asn Tyr Val Asn Asp Leu Val Pro Glu Phe Leu Pro Ala
65                  70                  75                  80

Pro Glu Asp Val Glu Thr Asn Cys Glu Trp Ser Ala Phe Ser Cys Phe
                85                  90                  95

Gln Lys Ala Gln Leu Lys Ser Ala Asn Thr Gly Asn Asn Glu Arg Ile
            100                 105                 110

Ile Asn Val Ser Ile Lys Lys Leu Lys Arg Lys Pro Pro Ser Thr Asn
        115                 120                 125

Ala Gly Arg Arg Gln Lys His Arg Leu Thr Cys Pro Ser Cys Asp Ser
    130                 135                 140

```
Tyr Glu Lys Lys Pro Pro Lys Glu Phe Leu Glu Arg Phe Lys Ser Leu
145                 150                 155                 160

Leu Gln Lys Met Ile His Gln His Leu Ser Ser Arg Thr His Gly Ser
            165                 170                 175

Glu Asp Ser

<210> SEQ ID NO 5
<211> LENGTH: 2142
<212> TYPE: DNA
<213> ORGANISM: Artificial Sequence
<220> FEATURE:
<223> OTHER INFORMATION: chemically synthesized

<400> SEQUENCE: 5
ggatccatgg actggacctg gattctgttc ctggtggccg ccgccaccag agtgcacagc      60
agagtgatgg gcatccagcg gaattgccag cacctgtgga gatggggcac catgatcctg     120
ggcatgatca tcatctgctc tgccgccgag aacctgtggg tgaccgtgta ctacggcgtg     180
cctgtgtgga aggacgccga gaccaccctg ttctgcgcca cgacgccaa ggcctacgat      240 accgaagtgc acaatgtgtg gccaccac gcctgcgtgc ctaccgatcc aacccccag       300 gagatcaacc tggagaacgt gaccgaggag ttcaacatgt ggaagaacaa catggtggag     360
cagatgcaca ccgacatcat cagcctgtgg gaccagagcc tgaagccttg cgtgaagctg     420 accccctctgt gcgtgaccct gaactgcagc aacgtgaacg tgaccaccaa catcatgaag    480
ggcgagatca gaactgcag cttcaacatg accaccgagc tgcgggacaa gaagcagaaa     540
gtgtacagcc tgttctacaa gctggacgtg gtgcagatca acaagagcaa cagcagcagc    600
cagtaccggc tgatcaactg caacaccagc gccatcaccc aggcctgccc caaagtgagc    660
ttcgagccca tccccatcca ctactgcgcc ctgccggct cgccatcct gaagtgcaag      720 gacaaggagt taacggcac cggcccctgc aagaatgtga gcaccgtgca gtgcacccac    780
ggcatcaagc ccgtggtgtc cacccagctg ctgctgaacg gcagcctggc cgaggaggaa   840
gtgatgatcc ggagcgagaa catcaccaac aacgccaaga acatcatcgt gcagctgacc   900
aagcccgtga gatcaattg cacccggccc aacaacaaca cccggaagag catcagaatc    960
ggccctggcc aggccttcta cgccaccggc gacatcatcg gcgatatcag gcaggcccac   1020
tgcaatgtga gccggaccga gtggaacgag accctgcaga agtggcaa gcagctgcgg      1080 aagtacttca caacaagac catcatcttc accaacagca gcggcggcag actgagaatc    1140
accacccaca gcttcaattg tggcggcgag ttcttctact gcaataccctc cggcctgttc   1200 aacagcacct ggaacggcaa cggcaccaag aagaagaaca gcaccgagag caacgacacc   1260
atcaccctgc cctgccggat caagcagatc atcaatatgt ggcagagggt gggccaggcc    1320
atgtacgccc ctcccatcca gggcgtgatc agatgcgaga gcaacatcac cggcctgctg    1380
ctgaccagag atggcggcga caacaacagc aagaacgaga ccttcagacc tggcggcgga    1440
gacatgaggg acaactggcg gagcgagctg tacaagtaca agtggtgaa gatcgagccc    1500 ctgggcgtgg ccccccaccaa ggccaagaga gagtggtgg agcgggagaa gagagctgtg    1560
ggcatcggcg ccgtgttcct gggcttcctg ggagccgccg aagcaccat gggagccgcc    1620 agcatcaccc tgaccgtgca ggccagacag ctgctgagcg gcattgtgca gcagcagagc    1680
aacctgctga gagccatcga ggcccagcag cacctgctga agctgacagt gtggggcatc    1740
aaacagctgc aggcccgcgt gctggccgtg gagagatacc tgaaggacca gcagctgctg    1800
ggcatctggg gctgcagcgg caagctgatc tgcaccacca acgtgccctg gaatagcagc   1860
```

```
tggagcaaca agagccagag cgagatctgg gacaacatga cctggctgca gtgggacaag    1920
gagatcagca actacaccga tatcatctac aacctgatcg aggagagcca agaaccagcag   1980 gagaagaacg agcaggatct gctggccctg gacaagtggg ccaacctgtg gaactggttc    2040
gacatcagca actggctgtg gtacatcaag atcttcatca tgattgtggg cggcctgatc    2100
ggcctgagaa tcgtgttcgc cgtgctgtct gtgtgactcg ag                       2142
```

<210> SEQ ID NO 6
<211> LENGTH: 709
<212> TYPE: PRT
<213> ORGANISM: Artificial Sequence
<220> FEATURE:
<223> OTHER INFORMATION: chemically synthesized

<400> SEQUENCE: 6

```
Met Asp Trp Thr Trp Ile Leu Phe Leu Val Ala Ala Thr Arg Val
1               5                   10                  15

His Ser Arg Val Met Gly Ile Gln Arg Asn Cys Gln His Leu Trp Arg
            20                  25                  30

Trp Gly Thr Met Ile Leu Gly Met Ile Ile Cys Ser Ala Ala Glu
            35                  40                  45

Asn Leu Trp Val Thr Val Tyr Tyr Gly Val Pro Val Trp Lys Asp Ala
50                  55                  60

Glu Thr Thr Leu Phe Cys Ala Ser Asp Ala Lys Ala Tyr Asp Thr Glu
65                  70                  75                  80

Val His Asn Val Trp Ala Thr His Ala Cys Val Pro Thr Asp Pro Asn
                85                  90                  95

Pro Gln Glu Ile Asn Leu Glu Asn Val Thr Glu Glu Phe Asn Met Trp
            100                 105                 110

Lys Asn Asn Met Val Glu Gln Met His Thr Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Ser Asn Val Asn Val Thr Thr Asn Ile Met Lys Gly Glu
145                 150                 155                 160

Ile Lys Asn Cys Ser Phe Asn Met Thr Thr Glu Leu Arg Asp Lys Lys
                165                 170                 175

Gln Lys Val Tyr Ser Leu Phe Tyr Lys Leu Asp Val Val Gln Ile Asn
            180                 185                 190

Lys Ser Asn Ser Ser Gln Tyr Arg Leu Ile Asn Cys Asn Thr Ser
        195                 200                 205

Ala Ile Thr Gln Ala Cys Pro Lys Val Ser Phe Glu Pro Ile Pro Ile
    210                 215                 220

His Tyr Cys Ala Pro Ala Gly Phe Ala Ile Leu Lys Cys Lys Asp Lys
225                 230                 235                 240

Glu Phe Asn Gly Thr Gly Pro Cys Lys Asn Val Ser Thr Val Gln Cys
                245                 250                 255

Thr His Gly Ile Lys Pro Val Val Ser Thr Gln Leu Leu Asn Gly
            260                 265                 270

Ser Leu Ala Glu Glu Val Met Ile Arg Ser Glu Asn Ile Thr Asn
        275                 280                 285

Asn Ala Lys Asn Ile Ile Val Gln Leu Thr Lys Pro Val Lys Ile Asn
    290                 295                 300

Cys Thr Arg Pro Asn Asn Asn Thr Arg Lys Ser Ile Arg Ile Gly Pro
```

```
            305                 310                 315                 320
        Gly Gln Ala Phe Tyr Ala Thr Gly Asp Ile Ile Gly Asp Ile Arg Gln
                        325                 330                 335

Ala His Cys Asn Val Ser Arg Thr Glu Trp Asn Glu Thr Leu Gln Lys
                        340                 345                 350

Val Ala Lys Gln Leu Arg Lys Tyr Phe Asn Asn Lys Thr Ile Ile Phe
                        355                 360                 365

Thr Asn Ser Ser Gly Gly Arg Leu Arg Ile Thr Thr His Ser Phe Asn
                    370                  375                 380

Cys Gly Gly Glu Phe Phe Tyr Cys Asn Thr Ser Gly Leu Phe Asn Ser
        385                 390                 395                 400

Thr Trp Asn Gly Asn Gly Thr Lys Lys Lys Asn Ser Thr Glu Ser Asn
                            405                 410                 415

Asp Thr Ile Thr Leu Pro Cys Arg Ile Lys Gln Ile Ile Asn Met Trp
                        420                 425                 430

Gln Arg Val Gly Gln Ala Met Tyr Ala Pro Pro Ile Gln Gly Val Ile
                        435                 440                 445

Arg Cys Glu Ser Asn Ile Thr Gly Leu Leu Leu Thr Arg Asp Gly Gly
            450                 455                 460

Asp Asn Asn Ser Lys Asn Glu Thr Phe Arg Pro Gly Gly Gly Asp Met
        465                 470                 475                 480

Arg Asp Asn Trp Arg Ser Glu Leu Tyr Lys Tyr Lys Val Val Lys Ile
                            485                 490                 495

Glu Pro Leu Gly Val Ala Pro Thr Lys Ala Lys Arg Arg Val Val Glu
                        500                 505                 510

Arg Glu Lys Arg Ala Val Gly Ile Gly Ala Val Phe Leu Gly Phe Leu
                        515                 520                 525

Gly Ala Ala Gly Ser Thr Met Gly Ala Ala Ser Ile Thr Leu Thr Val
                        530                 535                 540

Gln Ala Arg Gln Leu Leu Ser Gly Ile Val Gln Gln Ser Asn Leu
        545                 550                 555                 560

Leu Arg Ala Ile Glu Ala Gln Gln His Leu Leu Lys Leu Thr Val Trp
                        565                 570                 575

Gly Ile Lys Gln Leu Gln Ala Arg Val Leu Ala Val Glu Arg Tyr Leu
                        580                 585                 590

Lys Asp Gln Gln Leu Leu Gly Ile Trp Gly Cys Ser Gly Lys Leu Ile
                    595                 600                 605

Cys Thr Thr Asn Val Pro Trp Asn Ser Ser Trp Ser Asn Lys Ser Gln
        610                 615                 620

Ser Glu Ile Trp Asp Asn Met Thr Trp Leu Gln Trp Asp Lys Glu Ile
        625                 630                 635                 640

Ser Asn Tyr Thr Asp Ile Ile Tyr Asn Leu Ile Glu Glu Ser Gln Asn
                            645                 650                 655

Gln Gln Glu Lys Asn Glu Gln Asp Leu Leu Ala Leu Asp Lys Trp Ala
                        660                 665                 670

Asn Leu Trp Asn Trp Phe Asp Ile Ser Asn Trp Leu Trp Tyr Ile Lys
                    675                  680                 685

Ile Phe Ile Met Ile Val Gly Gly Leu Ile Gly Leu Arg Ile Val Phe
                    690                  695                 700

Ala Val Leu Ser Val
        705

<210> SEQ ID NO 7
```

<211> LENGTH: 2140
<212> TYPE: DNA
<213> ORGANISM: Artificial Sequence
<220> FEATURE:
<223> OTHER INFORMATION: chemically synthesized

<400> SEQUENCE: 7

| | |
|---|---|
| ggatccgcca ccatggattg gacctggatt ctgttcctgg tggccgccgc cacaagagtg | 60 |
| cacagcagag tgcggggcat cctgagaaat tgccagcagt ggtggatctg gggcattctg | 120 |
| gggttctgga tgctgatgat ctgcaacgtg atgggcaacc tgtgggtgac cgtgtactac | 180 |
| ggcgtgcctg tgtggaagga ggccaagacc accctgttct gtgccagcga tgccaaggcc | 240 |
| tacgagaccg aggtgcacaa tgtgtgggcc acccacgcct gtgtgccac cgatcccaac | 300 |
| cctcaggaga tggtgctgga gaacgtgacc gagaacttca acatgtggaa gaacgacatg | 360 |
| gtggaccaga tgcacgagga catcatcagc ctgtgggacc agagcctgaa gccttgcgtg | 420 |
| aagctgaccc ctctgtgcgt gaccctgaac tgcggaaca cgtgaacaa caacaacacc | 480 |
| atgaaggagg agatcaagaa ctgcagcttc aacatcacca ccgagctgcg ggacaagaag | 540 |
| cagaaggtgt acgccctgtt ctaccggctg gacatcgtgc ccctgaacga aagaacaac | 600 |
| agcaacgact accggctgat caactgcaac accagccgcca tcacccaggc ctgtcccaag | 660 |
| gtgtccttcg accccatccc catccactat tgtgccctg ccggctacgc catcctgaag | 720 |
| tgcaacaaca gaccttcaa cggcaccggc ccctgcaata atgtgagcac cgtgcagtgt | 780 |
| acccacggca tcaagcctgt ggtgtccacc cagctgctgc tgaatggcag cctggccgag | 840 |
| gaggagatta tcatccggag cgagaacctg accaacaacg ccaagaccat cattgtgcac | 900 |
| ctgaatgaga gcgtggagat cgtgtgtacc cggcccaaca caatacccg gaagagcatc | 960 |
| agaatcggcc ctggccagac cttttacgcc accggcgaca tcatcggcga tatcaggcag | 1020 |
| gcccactgca atatcagcga ggagaagtgg aacaagaccc tgcagcgggt gtccgagaag | 1080 |
| ctgaaggagc acttccccaa taagaccatc aagttcgccc tagcagcgg cggcagactg | 1140 |
| gagatcacca cccacagctt caactgcagg ggcgagttct tctactgcaa taccagcaag | 1200 |
| ctgttcaaca gcacctacat gcccaacagc accaacaata ccaacaccac catcaccctg | 1260 |
| ccctgccgga tcaagcagat catcaatatg tggcaggaag tgggcagagc catgtacgcc | 1320 |
| cctcccatcg agggcaacat cacctgcaag tccaacatca ccggcctgct gctgacaaga | 1380 |
| gatggcggca agaacgacac caatgacacc gagaccttca gacctggcgg cggagacatg | 1440 |
| agggacaact ggcggagcga gctgtacaag tacaaggtgg tggagatcaa gcctctgggc | 1500 |
| gtggccccta ccaaggccaa gaggagagtg gtggagaggg agaagagagc cgtgggcatc | 1560 |
| ggcgccgtgt ttctgggctt tctgggagcc gccggatcta caatgggagc cgccagcatc | 1620 |
| acactgaccg tgcaggccag acagctgctg agcggcatcg tgcagcagca gagcaatctg | 1680 |
| ctgagagcca tcgaggccca gcagcacatg ctgcagctga cagtgtgggg catcaagcag | 1740 |
| ctgcagacca gagtgctggc catcgagcgc tacctgaagg atcagcagct gctgggcatc | 1800 |
| tggggctgta gcggcaagct gatctgtacc accgccgtgc cttggaatag cagctggagc | 1860 |
| aacaagagcc aggaggacat ctgggacaac atgacctgga tgcagtggga ccggagatc | 1920 |
| agcaactaca ccgacaccat ctacaggctg ctggaggaca gcagaacca gcaggagaag | 1980 |
| aacgagaagg acctgctggc cctggacagc tggaagaacc tgtggaactg gttcgacatc | 2040 |
| accaactggc tgtggtacat caagatcttc atcatgattg tgggcggcct gatcggcctg | 2100 |
| agaatcatct tcgccgtgct gagcatctga tagcggccgc | 2140 |

<210> SEQ ID NO 8
<211> LENGTH: 705
<212> TYPE: PRT
<213> ORGANISM: Artificial Sequence
<220> FEATURE:
<223> OTHER INFORMATION: chemically synthesized

<400> SEQUENCE: 8

```
Met Asp Trp Thr Trp Ile Leu Phe Leu Val Ala Ala Thr Arg Val
1               5                   10                  15

His Ser Arg Val Arg Gly Ile Leu Arg Asn Cys Gln Gln Trp Trp Ile
                20                  25                  30

Trp Gly Ile Leu Gly Phe Trp Met Leu Met Ile Cys Asn Val Met Gly
            35                  40                  45

Asn Leu Trp Val Thr Val Tyr Tyr Gly Val Pro Val Trp Lys Glu Ala
50                  55                  60

Lys Thr Thr Leu Phe Cys Ala Ser Asp Ala Lys Ala Tyr Glu Thr Glu
65                  70                  75                  80

Val His Asn Val Trp Ala Thr His Ala Cys Val Pro Thr Asp Pro Asn
                85                  90                  95

Pro Gln Glu Met Val Leu Glu Asn Val Thr Glu Asn Phe Asn Met Trp
            100                 105                 110

Lys Asn Asp Met Val Asp Gln Met His Glu Asp Ile Ile Ser Leu Trp
        115                 120                 125

Asp Gln Ser Leu Lys Pro Cys Val Lys Leu Thr Pro Leu Cys Val Thr
    130                 135                 140

Leu Asn Cys Arg Asn Asn Val Asn Asn Asn Thr Met Lys Glu Glu
145                 150                 155                 160

Ile Lys Asn Cys Ser Phe Asn Ile Thr Thr Glu Leu Arg Asp Lys Lys
                165                 170                 175

Gln Lys Val Tyr Ala Leu Phe Tyr Arg Leu Asp Ile Val Pro Leu Asn
            180                 185                 190

Glu Lys Asn Asn Ser Asn Asp Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Asn Gly
            260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Ser Val Glu Ile Val
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Ile Ser Glu Glu Lys Trp Asn Lys Thr Leu Gln Arg
            340                 345                 350

Val Ser Glu Lys Leu Lys Glu His Phe Pro Asn Lys Thr Ile Lys Phe
        355                 360                 365
```

```
Ala Pro Ser Ser Gly Gly Arg Leu Glu Ile Thr Thr His Ser Phe Asn
    370                 375                 380

Cys Arg Gly Glu Phe Phe Tyr Cys Asn Thr Ser Lys Leu Phe Asn Ser
385                 390                 395                 400

Thr Tyr Met Pro Asn Ser Thr Asn Asn Thr Asn Thr Thr Ile Thr Leu
                405                 410                 415

Pro Cys Arg Ile Lys Gln Ile Ile Asn Met Trp Gln Glu Val Gly Arg
            420                 425                 430

Ala Met Tyr Ala Pro Pro Ile Glu Gly Asn Ile Thr Cys Lys Ser Asn
            435                 440                 445

Ile Thr Gly Leu Leu Leu Thr Arg Asp Gly Gly Lys Asn Asp Thr Asn
    450                 455                 460

Asp Thr Glu Thr Phe Arg Pro Gly Gly Gly Asp Met Arg Asp Asn Trp
465                 470                 475                 480

Arg Ser Glu Leu Tyr Lys Tyr Lys Val Val Glu Ile Lys Pro Leu Gly
                485                 490                 495

Val Ala Pro Thr Lys Ala Lys Arg Arg Val Val Glu Arg Glu Lys Arg
            500                 505                 510

Ala Val Gly Ile Gly Ala Val Phe Leu Gly Phe Leu Gly Ala Ala Gly
            515                 520                 525

Ser Thr Met Gly Ala Ala Ser Ile Thr Leu Thr Val Gln Ala Arg Gln
    530                 535                 540

Leu Leu Ser Gly Ile Val Gln Gln Gln Ser Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Thr Arg Val Leu Ala Ile Glu Arg Tyr Leu Lys Asp Gln Gln
            580                 585                 590

Leu Leu Gly Ile Trp Gly Cys Ser Gly Lys Leu Ile Cys Thr Thr Ala
            595                 600                 605

Val Pro Trp Asn Ser Ser Trp Ser Asn Lys Ser Gln Glu Asp Ile Trp
    610                 615                 620

Asp Asn Met Thr Trp Met Gln Trp Asp Arg Glu Ile Ser Asn Tyr Thr
625                 630                 635                 640

Asp Thr Ile Tyr Arg Leu Leu Glu Asp Ser Gln Asn Gln Gln Glu Lys
                645                 650                 655

Asn Glu Lys Asp Leu Leu Ala Leu Asp Ser Trp Lys Asn Leu Trp Asn
            660                 665                 670

Trp Phe Asp Ile Thr Asn Trp Leu Trp Tyr Ile Lys Ile Phe Ile Met
            675                 680                 685

Ile Val Gly Gly Leu Ile Gly Leu Arg Ile Ile Phe Ala Val Leu Ser
    690                 695                 700

Ile
705

<210> SEQ ID NO 9
<211> LENGTH: 9
<212> TYPE: PRT
<213> ORGANISM: Artificial Sequence
```

```
<220> FEATURE:
<223> OTHER INFORMATION: chemically synthesized

<400> SEQUENCE: 9

Tyr Pro Tyr Asp Val Pro Asp Tyr Ala
1               5
```